United States Patent [19]
Li et al.

[11] Patent Number: 5,874,310
[45] Date of Patent: Feb. 23, 1999

[54] METHOD FOR DIFFERENTIATION OF NUCLEATED RED BLOOD CELLS

[75] Inventors: Yi Li; Jing Li; Carole Young, all of Miami, Fla.

[73] Assignee: Coulter International Corp., Miami, Fla.

[21] Appl. No.: 975,846

[22] Filed: Nov. 21, 1997

[51] Int. Cl.$^6$ ........................................... G01N 31/00
[52] U.S. Cl. .............. 436/10; 436/63; 436/164; 436/175
[58] Field of Search .................. 436/10, 63, 164, 436/175; 435/2

[56] References Cited

U.S. PATENT DOCUMENTS

| | | | |
|---|---|---|---|
| 4,284,412 | 8/1981 | Hansen et al. ................. | 356/39 X |
| 4,735,504 | 4/1988 | Tycko ............................. | 356/336 |
| 5,125,737 | 6/1992 | Rodriguez et al. ............. | 356/39 |
| 5,155,044 | 10/1992 | Ledis et al. .................... | 436/17 |
| 5,298,426 | 3/1994 | Inami et al. .................... | 436/63 |
| 5,389,549 | 2/1995 | Hamaguchi et al. ........... | 436/10 |
| 5,510,267 | 4/1996 | Marshall et al. ............... | 436/63 |
| 5,559,037 | 9/1996 | Kim et al. ....................... | 436/63 |
| 5,631,165 | 5/1997 | Chupp et al. ................... | 436/43 |
| 5,648,225 | 7/1997 | Kim et al. ....................... | 435/7.24 |
| 5,686,308 | 11/1997 | Li et al. .......................... | 436/63 |
| 5,737,078 | 4/1998 | Takarada et al. ............... | 356/338 |
| 5,776,709 | 7/1998 | Jackson et al. ................. | 435/7.24 |

*Primary Examiner*—Maureen M. Wallenhorst
*Attorney, Agent, or Firm*—Mitchell E. Alter

[57] ABSTRACT

A method is provided for differentiation of nucleated red blood cells. In addition, the method provides for a concurrent differentiation of leukocytes in a blood cell sample by suitable electronic and optical measurements. The method includes exposing a blood cell sample to a reagent system to lyse mature red blood cells and subsequently analyzing nucleated red blood cells in a flow cell by optical analysis. A concurrent differentiation of nucleated blood cells and leukocytes can be performed using electronic and optical analysis. The electronic and optical analysis includes light scatter and impedance measurements. This method eliminates the use of nuclear stain for identification of nucleated red blood cells. The method of the present invention, for the first time, reports differentiation and enumeration of nucleated red blood cells without using fluorescence.

18 Claims, 8 Drawing Sheets

METHOD FOR DIFFERENTIATION OF NUCLEATED RED BLOOD CELLS

FIELD OF THE INVENTION

The present invention relates to a method for the differentiation of nucleated red blood cells. In addition, the method provides for a concurrent differentiation of leukocytes in a blood cell sample by suitable electronic and optical measurements.

BACKGROUND OF THE INVENTION

Normal peripheral blood contains mature red blood cells which are free of nucleus and reticulum. Nucleated red blood cells (NRBCs), or erythroblasts, are immature red blood cells. They normally occur in the bone marrow but not in peripheral blood. However, in certain diseases such as anemia and leukemia, NRBCs also occur in peripheral blood. Therefore, it is of clinical importance to measure NRBC. Traditionally, differentiation and enumeration of NRBC are performed manually. The process involves the smearing of a blood sample on a microscope slide and staining the slide, followed by manual visual analysis of the individual slide. The NRBC concentration is reported as number of NRBCs per 100 white blood cells. Usually, 200 white blood cells and the number of NRBCs present in the same region on a blood smear are counted and the numbers are divided by 2 to express the NRBC concentration as the number of NRBCs/100 white blood cells. This approach is extremely time-consuming as well as being subjective to the interpretation of the individual analyzing the slide.

In recent years, several fluorescence flow cytometry methods have been developed for differentiating NRBCs. These methods utilizes specific nuclear staining technique to distinguish NRBCs from other cell populations because it is not easy to differentiate NRBCs based on their electronic or optical properties.

U.S. Pat. No. 5,298,426 (to Inami et al.) discloses a fluorescence method for differentiating NRBCs. The method utilizes a two-step staining using a first fluid which is an acidic hypotensive fluorescent dye solution, and a second fluid which changes the osmolality and pH of the first fluid. Inami et al. teaches that the first fluid contains an erythroblast-staining dye that diffuses into nucleated red blood cells to specifically stain their nuclei, and then separating a group of NRBCs from other cell groups on a two-dimensional plot whereby the results of NRBC differentiation are computed. In order to differentiate leukocyte subpopulation concurrently, the first fluid also contains two additional fluorescence dyes, i.e., an eosinophil/basophil-staining dye and leukocyte-staining dye for specific staining of these cell types.

U.S. Pat. No. 5,559,037 (to Kim et al.) discloses a method for flow cytometric analysis of NRBCs and leukocytes. The method comprises lysis of red blood cells and NRBC cytoplasm from a whole blood sample to expose the NRBC nuclei to a vital nuclear stain and minimizing the permeation of the vital nuclear stain into the leukocytes and analyzing the sample by measuring fluorescence and two angles of light scatter. This method features a triple triggering method which blocks the signals from debris (fluorescent and non-fluorescent) and identifies the signals which fall below the ALL trigger but above the fluorescence trigger (FL3) as NRBCs. ALL is the axial loss of light or the light scatter signals detected at 0° from the incident light. Therefore, pre-gating signals in more than one dimension are required in this method for identification of NRBC population. Since leukocytes are also nucleated cells, staining of these cells needs to be prevented to avoid interference to the fluorescence measurement. The preservation of leukocyte membrane and minimizing the permeation of the nuclear stain into the leukocytes are achieved by concurrently fixing the leukocytes with an aliphatic aldehyde during lysis of red blood cells. The aldehyde fixatives are known as hazardous chemicals. In addition, the method requires heating of the reagent to 42° C. in order to obtain the NRBC and leukocyte differentiations.

The above described methods are able to differentiate and enumerate NRBCs and leukocytes by fluorescence flow cytometry. However, fluorescence measurement is a complex and expensive detection method.

Current automated hematology analyzers, such as Abbott Cell-Dyn®3500, COULTER® STKS®, Technicon H*1® and TOA Sysmex™ NE-8000 are only able to provide NRBC flagging for the possible presence of NRBCs in an analyzed blood sample when the instruments sense an increased amount of signals near red blood cell debris area of a histogram. However, such techniques frequently generate false positive flagging because many other blood abnormalities can cause increased signals at the same area, such as platelet clumps and sickle cells, as well as red cell debris from insufficiently lysed blood samples. In these methods NRBCs are not identified. Instead, only a common NRBC sample distribution pattern in a histogram or a dotplot is recognized by the instrument which can be easily confused with a similar pattern generated by above-mentioned other causes. For the flagged samples, including false positive flags, re-examination of the sample with manual method is required in clinical laboratories. Another problem with the NRBC containing samples is that the white blood cell count (WBC) reported by hematology analyzers is not accurate for these samples since NRBCs could elevate the WBC by being misidentified as white cells. On the other hand, analysis of leukocyte populations from whole blood samples is an integral part of diagnostic procedures regarding a multiplicity of pathologies. The ability to analyze the major subpopulations of leukocytes in an automated manner is essential for a rapid diagnosis of a single blood sample and for the rapid processing of many samples at once.

U.S. Pat. No. 5,155,044 (to Ledis et al.) discloses a method for isolation and analysis of leukocytes from a whole blood sample, which enables differentiation of leukocytes into five subpopulations in a one-step measurement on an automated hematology analyzer. The detection technique involves a concurrent light scatter measurement and impedance measurements in both DC (direct current) and RF (radio frequency). This method is simple and fast, but it does not provide differentiation of NRBCs.

U.S. Pat. No. 5,389,549 (to Hamaguchi et al.) describes a lysis reagent system and a method for differentiation of leukocytes into five subpopulations by a complex procedure. The method requires three lytic reagents, three separate sample preparations and measurements for the identity of eosinophil, neutrophil and basophil populations in addition to the lymphocyte and monocyte populations. Hamaguchi et al. describe merely the observation of abnormal leukocyte populations and nucleated red blood cells using the lysis reagent system and DC vs. RF detection method. However, this method is limited to only observing the presence of some abnormal cell types, but is not able to differentiate or enumerate the NRBCs.

U.S. Pat. No. 5,686,308 (to Li et al.) describes a lysing reagent system and a method for differentiation of leukocytes into five subpopulations in a one-step measurement on an automated hematology analyzer. The lytic reagent comprises a lytic reagent comprising an ethoxylated long chain amine compound and acid to adjust the pH of the lytic reagent to be within the range of 2.0 to 3.6; and a hypertonic, alkaline stabilizing reagent. This patent teaches a reagent and method for differentiation of leukocytes subpopulations, but does not teach differentiation of nucleated red blood cells.

Based on foregoing, there exist a need for a simple and less costly analysis method for differentiating and enumerating NRBCs.

SUMMARY OF THE INVENTION

One object of the present invention is to provide a method which permit the differentiation of nucleated red blood cells on an automated hematology analyzer without using fluorescence or nuclear stain. The method comprises exposing a blood cell sample to a reagent system to lyse mature red blood cells; analyzing said sample in a flow cell by light scatter measurement to differentiate nucleated red blood cells; and reporting nucleated red blood cells in said blood cell sample.

Another object of the present invention is to provide a method which permits a concurrent differentiation of nucleated red blood cells and leukocytes. The method comprises exposing a blood cell sample to a reagent system to lyse mature red blood cells without damaging leukocytes; analyzing the sample in a flow cell by DC and light scatter measurements to differentiate nucleated red blood cells and leukocyte subpopulations; and reporting NRBCs and leukocyte subpopulations in the blood cell sample.

As will be better appreciated from the ensuing Detailed Description of Preferred Embodiments, the invention is particularly advantageous compared to the prior art in that it provides differentiation of nucleated red blood cells utilizing light scatters without nuclear staining and the use of complex fluorescence detection method. An additional feature of the present method is that it does not require heating for sample preparation and operates optimally at room temperature. The invention will be better understood from the ensuing description of preferred embodiments.

BRIEF DESCRIPTION OF THE DRAWINGS

FIGS. 1–7 are scattergrams obtained in accordance with the practice of the present invention as described in Examples I to VI.

DETAILED DESCRIPTION OF THE PREFERRED EMBODIMENTS

Figure 1:
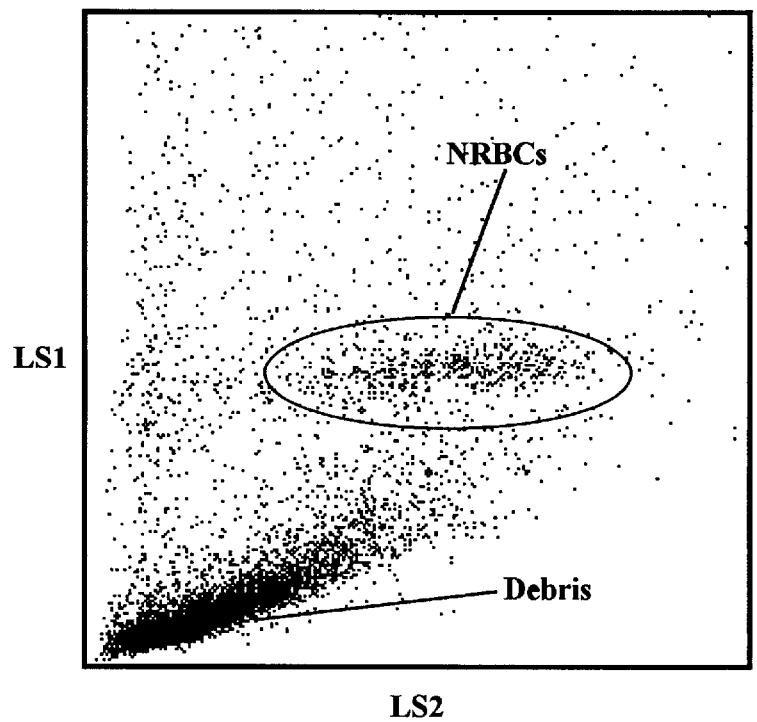

The present invention relates to a method for differentiation of NRBCs. In addition, the method provides for a concurrent differentiation of leukocytes in a blood cell sample.

In a first embodiment, the method of the present invention comprises exposing a blood cell sample to a reagent system to lyse mature red blood cells; subsequently analyzing the sample mixture in a flow cell using light scatters to differentiate NRBCs; and reporting NRBCs in the blood cell sample.

One reagent system suitable for the present invention comprises a lytic reagent comprising an ethoxylated long chain amine compound represented by the general formula:

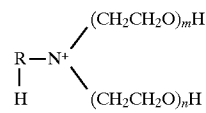

wherein R is an alkyl, alkenyl or alkynyl group having 12 to 22 carbon atoms, m and n are each 1 or more and m+n is between 20 and 40, and acid to adjust the pH of the lytic reagent to be within the range of 2.0 to 3.6; and a hypertonic, alkaline stabilizing reagent.

Optionally, one or more solubilizers can be included in the lytic reagent in an amount effective to reduce red blood cell debris. Typically, the solubilizers are polyoxyethylene and polyoxypropylene copolymers, and ethoxylated alcohols having a HLB of 16 or greater. Suitable copolymers include, but are not limited to, Pluronic copolymer (BASF Corporation, Parsippany, N.J.) such as Pluronic F38 and Pluronic 25R8, and suitable ethoxylated alcohols include, but are not limited to, Plurafac A38 (BASF) and Hetoxol STA 30 (Heterene, Inc. Paterson, N.J.).

Additional optional additives can also be included in the lytic reagent in concentrations that their presence is compatible with the primary functional components of the lytic reagent composition. Among these additives are preservatives which have anti-oxidant properties, to increase the shelf-life of the composition, and which have anti-microbial properties. Preservatives which have anti-oxidant properties include, but are not limited to, EDTA and butylmethylphenol. Preservatives which have anti-microbial activity include but are not limited to dimethyloldimethyl hydantoin, iodopropynylbutyl carbamate and isothiozolone derivatives.

Another reagent system that can be used for the method of the present invention is disclosed in U.S. Pat. No. 5,155,044. This reagent system utilizes a hypotonic acid lyse to selectively lyse red blood cells and a subsequently added quenching solution to retard the lysing activity and protect leukocytes for differential analysis.

The differential analysis of NRBCs is performed in a flow cell with a sheath fluid using light scatter measurements. When a particle, such as a blood cell, passes through the aperture of a flow cell, it scatters the incident light from a laser beam in all directions. The light scatter signals can be detected by a light detector at various angles relative to the incident light beam between 0° to 180°. It has been found that each cell population has different light scattering properties, either significant or minor, which might be utilized for differentiation of different cell populations. The light scatter signals detected in less than 10° from the incident light is commonly called low angle light scatter. The characteristics of low angle light scatter are affected by the size of a cell as well as the contents of a cell.

Light scatter signal from a particle or a cell passing through the flow cell is used for the purposes of the present invention. Preferably, two angles of light scatter signals are used for differentiation of NRBCs. More preferably, both angles of light scatter are less than 10°. The more preferred range of the first angle is from about 0° to about 4°. The more preferred range of the second angle is from about 3° to about 7°.

Figure 2:
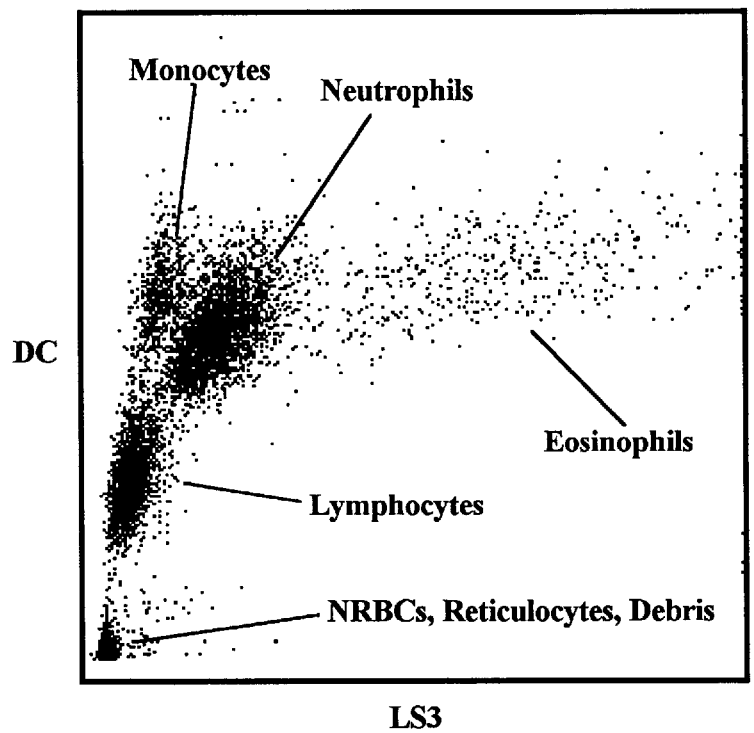

FIG. 1 shows an LS1 (1°–3°) vs. LS2 (4°–6°) scattergram of a clinical whole blood sample, containing 14 NRBC /100 WBC processed and analyzed following the procedure described in Example I. In this scattergram, NRBCs form a cluster which are clearly distinguished from red blood cell debris which is noted below the NRBCs and are clearly distinguished from leukocytes (which are out of the scope of this scattergram). In the DC scale, the NRBC populations, described in FIG. 1, are below lymphocytes in a region that is usually considered a debris region as shown in FIG. 2.

Figures 4A, 4B:
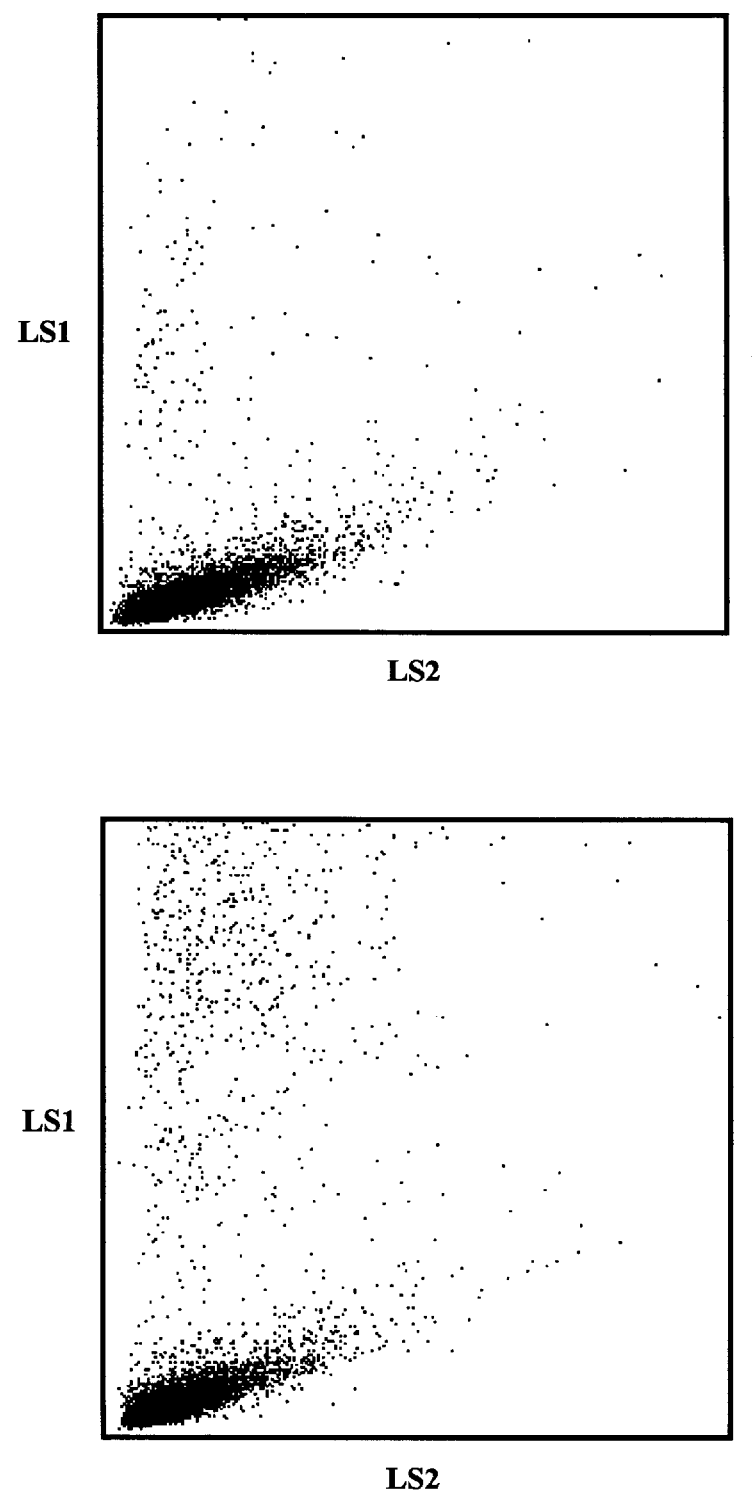

FIG. 4A shows an LS1 vs. LS2 scattergram, in an identical scales as FIG. 1, which is obtained from a normal fresh whole blood sample processed and analyzed following the procedure described in Example IV. As can readily be seen, there is no cluster present in the region where NRBCs appear (as shown in FIG. 1) because a normal peripheral blood does not have NRBCs. The same sample was kept at room temperature (about 23° C.) for about thirty hours and then processed and analyzed again using the same procedure. FIG. 4B shows the resultant scattergram. No cluster is found in the scattergram at the NRBC region. This illustrates that the method of the present invention has a low risk of reporting false positive results for normal blood samples even when the samples are aged.

It is very important that aged blood samples do not interfere with NRBC detection. Blood cells in an aged blood sample are more fragile and more sensitive to lysing conditions. Upon exposing an aged blood sample to a lytic reagent, cytoplasm or cell membrane of some leukocytes is also destructed. The partially exposed leukocyte nuclei will also be stained by nuclear stain when a fluorescence method is used for analysis of NRBC. Their fluorescence signals will be detected also. The signals from NRBCs and stained leukocytes usually overlap with each other. Therefore, it is more difficult to differentiate NRBC from other cell types in aged blood samples using a fluorescence method. With the method of the present invention, the fragile leukocytes do not intrude into or overlap with the NRBC cluster. Therefore, it is readily apparent that the present invention is advantageous in detecting NRBCs in aged blood samples.

Figure 5:
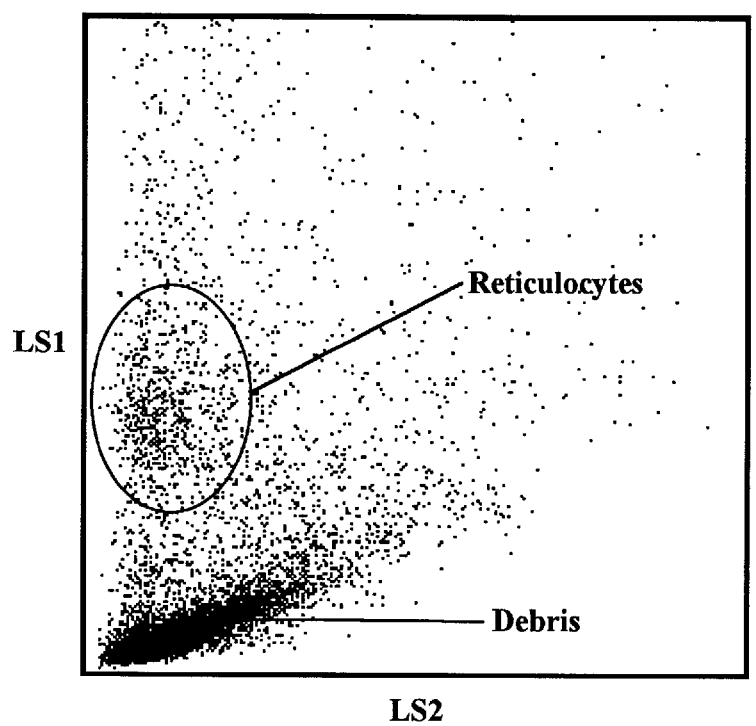

FIG. 5 shows a scattergram obtained from a clinical sample containing 5% reticulocytes analyzed using the method of the present invention described in Example V. The scattergram shows an additional cluster to the left of NRBCs, which corresponds to reticulocytes. Reticulocyte is another type of immature red blood cell which does not contain nuclei, but contains RNA. Different from NRBCs, reticulocytes appear in both the bone marrow and peripheral blood. In certain diseases, such as hemolytic anemia, thalassemia, and sideroblastic anemia, increased reticulocytes occur. Most nuclear stains used for staining NRBCs also stain RNA in reticulocytes. The staining of reticulocytes generates fluorescence signals which overlap with the NRBC fluorescence signals. Therefore, the NRBC results could be erroneous using a fluorescence method if no specific correction is performed for the reticulocytes.

Figure 6:
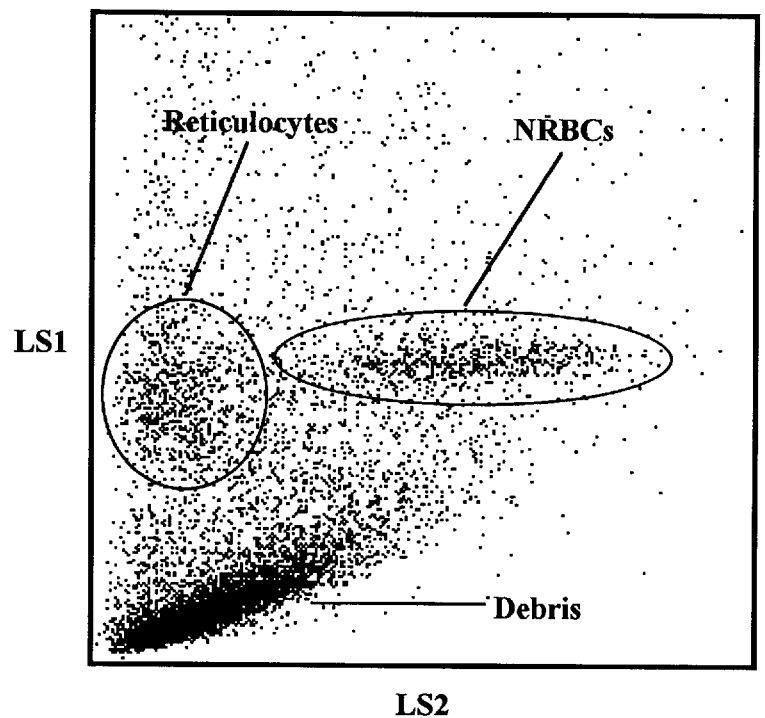

FIG. 6 shows a scattergram of a clinical sample containing both NRBCs and reticulocytes. The sample was analyzed using the same procedure of Example V. The NRBC report is consistent with the result of the manual reference. Therefore, the presence of reticulocytes does not interfere with the NRBC measurement using the method of the present invention.

The differentiation of NRBCs by low angle light scatters (LS1 and LS2) is simple and straightforward. It utilizes a regular two-dimensional dotplot, or scattergram, to distinguish NRBCs from other cell types. Because in previous methods, NRBC signals overlap with the signals from red blood cell debris and other cell types, such as leukocytes and reticulocytes, in one or more dimensions, prior art methods require pre-gating or multiple gating of the detected fluorescence and light scatter signals for identifying NRBC population. The present method does not need pre-gating or editing of the detected signals since NRBCs are separated from other cell types including red blood cell debris by the two-dimensional detection method.

The cell populations above the NRBC cluster in LSI are counted as total leukocytes (WBC). In addition, another method can be used to determine total leukocytes (WBC). If a DC detection device is also used, the cell populations above the minimum DC volume of the lymphocytes, can be counted as total leukocytes. The WBC obtained in both of these methods is free of NRBCs interference, and is equivalent to the corrected WBC, which is generated by subtracting a manual NRBC count from a WBC produced by a regular commercial blood counter.

The NRBC concentration of the analyzed sample can be calculated by dividing the number of cells counted in the identified NRBC cluster (FIG. 1) by the total leukocytes (WBC) counted and multiplying the quotient by 100. The NRBC concentration can be reported as the number of NRBC/100 WBC, which is the same as the manual report unit, or can be reported as an absolute NRBC per $\mu$l of a whole blood.

In a second embodiment of the present invention, a differential analysis of leukocytes can be performed together with the differentiation of NRBCs. The differential analysis can be performed using the same reagent system and one sample preparation, in a one step measurement using electronic and optical analysis. The electronic and optical analysis includes light scatter and impedance measurements. The DC impedance measurement device used for leukocyte analysis by an automated hematology analyzer is known to those skilled in the art and is generally described in U.S. Pat. No. 5,125,737, to Rodriguez et al., which is hereby incorporated by reference in its entirety. For differential analysis of NRBC and leukocytes a light scatter detector capable of detecting low and medium angle light scatter signals from a particle or a cell passing through the flow cell is used.

In FIG. 1, leukocytes are out of the range of the LS1 vs. LS2 scattergram, and are not shown in this figure. However, the sample analysis for leukocyte differentiation and NRBC differentiation can be performed in an one step measurement. The data analysis for both differentiations can be performed simultaneously using different parameters obtained from the one step measurement.

FIG. 2 is a DC vs. LS3 (medium angle light scatter, from about 24° to about 35°) scattergram obtained from a fresh normal whole blood sample processed according to Example II (the same reagents and procedure used in Example I). FIG. 2 shows four distinct clusters of leukocyte subpopulations, lymphocytes, monocytes, neutrophils and eosinophils. The sample was processed in one sample preparation and analyzed simultaneously with NRBC differentiation. In the DC vs. LS3 scattergram, all cell populations above the minimum DC volume of lymphocyte population are counted as total leukocytes (WBC), which is equivalent to the populations above the NRBC cluster in the LS1 vs. LS2 scattergram.

The method of the present invention, for the first time, reports the differentiation and enumeration of nucleated red blood cells without using nuclear stain and fluorescence. Elimination of nuclear staining provides advantages in reducing instrument and fluid system maintenance because of dye contamination, reducing system's sensitivity to reagent carry-over and reducing reagent cost due to expensive fluorescent dyes. The method of the present invention is fast, reliable and suitable for automated blood analysis. In addition, the detection technique is less complex and inexpensive compared to fluorescence method.

The method of the present invention also provides an advantage of operating entirely at room temperatures, 18° to 28° C. Prior art methods operate at elevated temperature for differentiation of leukocyte subpopulations or differentiation of NRBCs. This elevated temperature requirement necessitates analysis instrumentation which is significantly more complex because the reactions must be thermostatically controlled. The present invention overcomes this need for thermostatic control by operating optimally at room temperature.

Another advantageous feature of this invention is its utility for differential analysis of other fluid samples, such as bone marrow, and blood samples of non-human species. Example VI provides an example for application of the present method in veterinary sample NRBC analysis.

The method of this invention can be further understood by reference to the following examples. However, it will be appreciated that the invention is not limited to the described examples.

EXAMPLE I

To 28 μl of an EDTA-anticoagulated clinical whole blood sample 417 μl of a lytic reagent comprising 0.18% formic acid, 2% of ethoxylated long chain amine represented by formula:

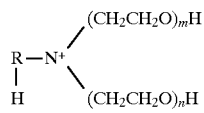

wherein R is stearyl and m+n is equal to 27, 1.4% of Plurafac A38 as a solubilizer and preservatives were added and mixed in a mixing chamber on an experimental hematology analyzer for about 4 seconds. Then 180 μl of a stabilizing reagent comprising 1.4% NaCl, 3.2% $Na_2SO_4$ and 0.66% $Na_2CO_3$, and having a pH of 11.0 was added and mixed to retard the lytic reaction.

Ten seconds after the addition of the stabilizing reagent the sample mixture was delivered to a flow cell with a sheath fluid, ISOTON® III diluent (product of Coulter Corporation, Miami, Fla.), for NRBC and leukocyte differential analysis on an experimental hematology analyzer equipped with DC and light scatter detectors. The light scatter detector detects light scatter signals from a cell passing through the flow cell at several ranges of angles, i.e., from about 1° to about 3° (LS1), from about 4° to about 6° (LS2), from about 24° to about 35° (LS3) and higher angles.

The resultant scattergrams are illustrated in FIG. 1. FIG. 1 shows a cluster of NRBC distinguished from red cell debris (below) and leukocytes (above, but out of the scope of the scattergram) in an LS1 vs. LS2 scattergram.

The NRBC concentration of the analyzed sample is calculated by dividing the number of cells counted in the identified NRBC cluster (FIG. 1) by the total leukocytes (WBC) counted and multiplying the quotient by 100. The NRBC concentration is reported as number of NRBC/100 WBC, which is the same as the manual report unit. For this sample both the manual reference method and the method described above reported 14 NRBC/100 WBC.

EXAMPLE II

A fresh normal whole blood sample was analyzed using the same reagents and procedure described in Example I. The sample mixture was analyzed simultaneously in the flow cell on the same hematology analyzer used in Example I for leukocyte differentiation and NRBC differentiation. FIG. 2 is an obtained DC vs. LS3 scattergram, which shows four distinct clusters of leukocyte subpopulations, lymphocytes, monocytes, neutrophils and eosinophils.

EXAMPLE III

To 28 μl of an EDTA-anticoagulated clinical whole blood sample 449 μl of a lytic reagent composed of 0.12% formic acid and 0.07% of saponin were added and mixed in a mixing chamber on a hematology analyzer for about 5 seconds. Then 177 μl of the same stabilizing reagent described in Example I were added and mixed to inhibit the lytic reaction.

Figure 3:
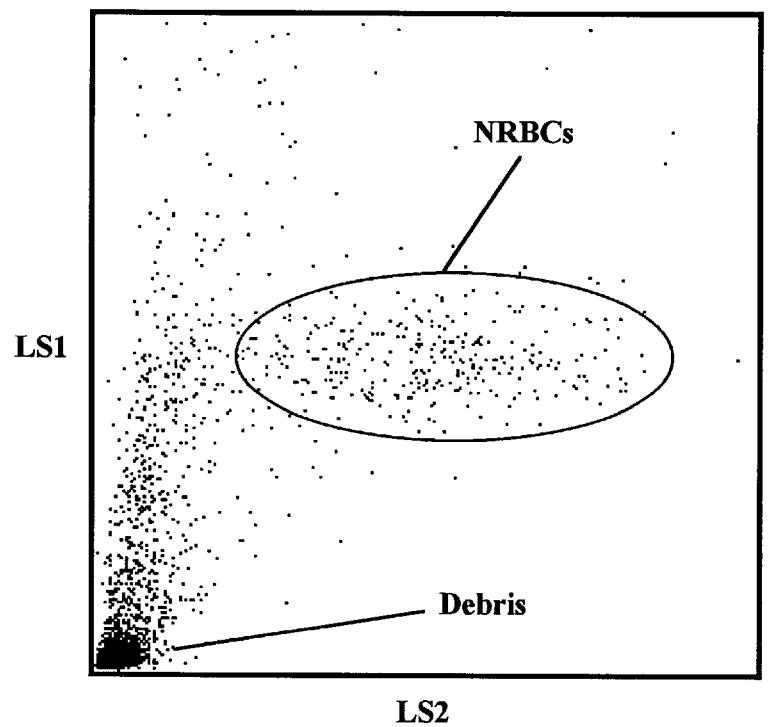

About 8 seconds after the addition of the stabilizing reagent, the sample mixture was delivered to a flow cell with a sheath fluid, ISOTON® III diluent for NRBC and leukocyte differential analysis on the same hematology analyzer described in Example I. FIG. 3 is the resultant LS1 vs. LS2 scattergram (in the same scale as in FIG. 1) which shows the NRBC cluster separated from other cell types.

EXAMPLE IV

The reagent and procedure described in Example I were used for analysis of a fresh normal whole blood sample. The sample was kept at room temperature (about 23° C.) for about thirty hours and then processed and analyzed again. The resultant scattergrams are shown in FIG. 4A for fresh blood and FIG. 4B for aged blood. In FIG. 4A, no cluster is present in the region where NRBCs appear because a normal peripheral blood does not contain NRBCs. No cluster is found either in FIG. 4B at the NRBC region. This example shows that the method of the present invention has a low risk in reporting false positive results for normal blood samples even when the normal blood samples are aged.

EXAMPLE V

The procedure and reagent described in Example I were used for analysis of a blood sample containing reticulocytes (5% reported by manual reference). FIG. 5 is the resultant LS1 vs. LS2 scattergram. It shows an additional cluster on the left of NRBCs, which corresponds to reticulocytes. FIG. 6 shows a scattergram obtained from a clinical sample containing both NRBCs and reticulocytes using the same procedure. The NRBC report was consistent with the manual reference result, 17 NRBC/100 WBC from the method of the present invention vs. 16 NRBC/100 WBC from the manual reference.

EXAMPLE VI

Figure 7:
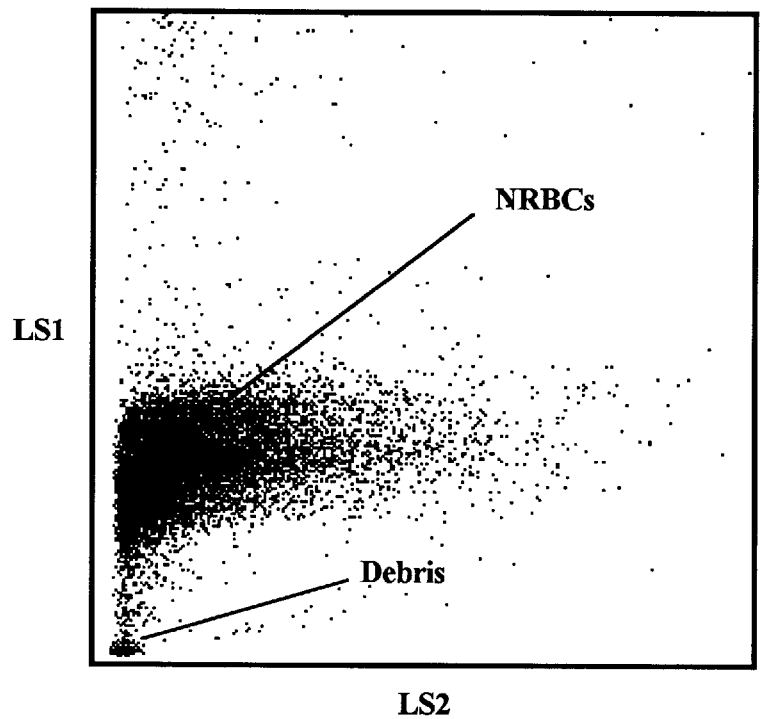

4 μl of an alligator blood was mixed with 4.15 ml of the lytic reagent of Example I in a test tube manually for about 4 seconds. 1.8 ml of the stabilizing reagent of Example I was added and the sample mixture was mixed manually and introduced to the hematology analyzer described in Example I. FIG. 7 is the obtained LS1 vs. LS2 scattergram. As shown, the NRBCs formed a distinct cluster.

EXAMPLE VII

Figure 8:
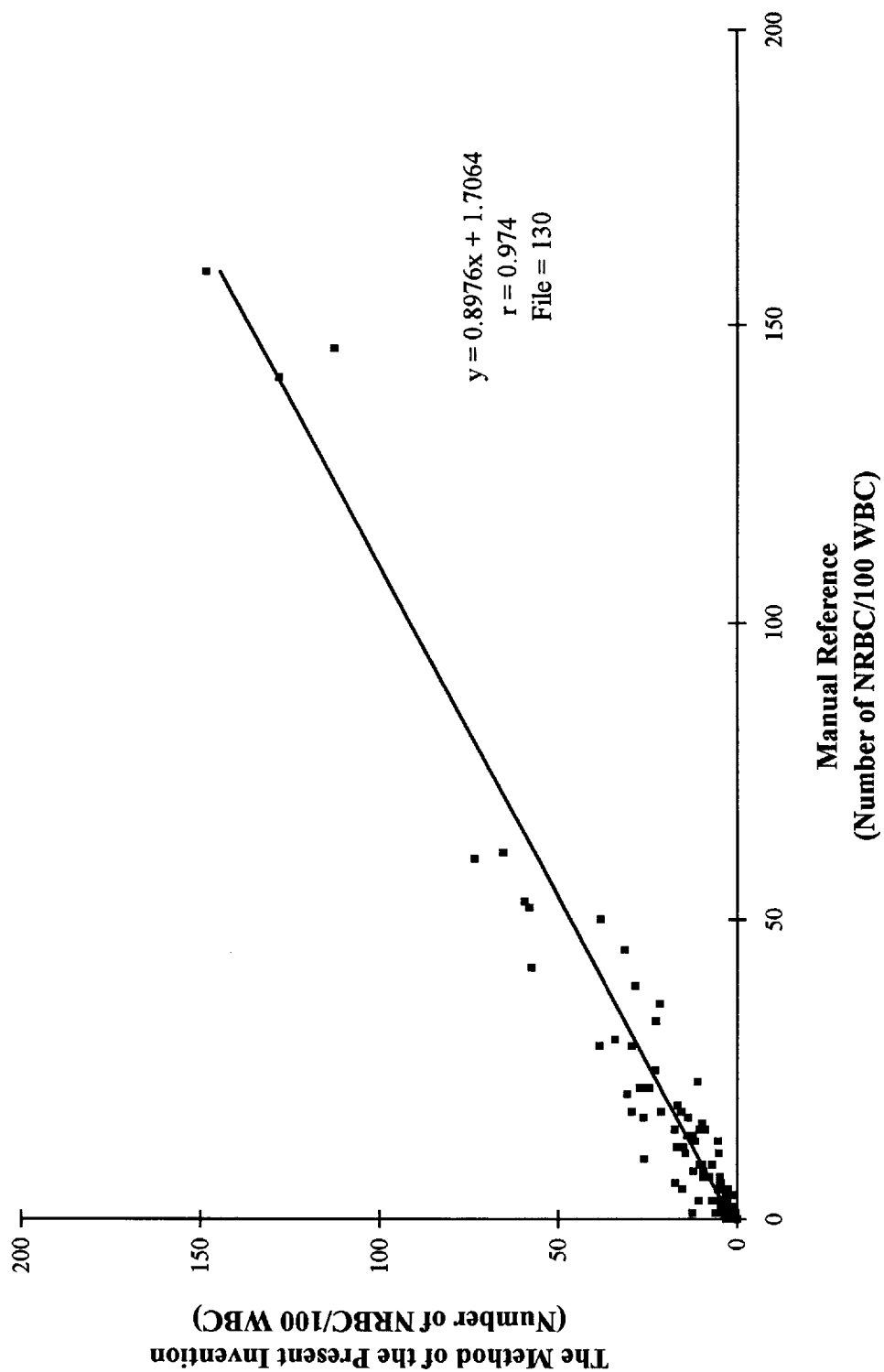
FIG. 8 is a curve illustrating the correlation between results obtained by the manual reference method and the method of the present invention as described in Example VII.

Total of 130 whole blood samples including 84 of clinical samples were analyzed using the method of this invention and the lytic reagent of Example I. The NRBCs of these samples were also counted using the reference manual method. For manual NRBC count, 200 WBC were counted on each patient's blood smear stained with Wright stain, and the number of NRBCs present in the same region were counted and divided by two to report NRBC/100 WBC. FIG. 8 shows the correlation between the manual reference method and the method of the present invention. The correlation coefficient is 0.974, the slope is 0.90 and intercept is 1.71.

The invention has been described with reference to particularly preferred embodiments. It will be appreciated, however, that various changes can be made without departing from the spirit of the invention, and such changes are intended to fall within the scope of the appended claims.

What is claimed is:

1. A method for differentiating nucleated red blood cells comprising:
   (a) exposing a blood cell sample to a reagent system to lyse mature red blood cells;
   (b) analyzing said sample in a flow cell by light scatter measurement to differentiate nucleated red blood cells from other cell types; and
   (c) reporting nucleated red blood cells in said blood cell sample.

2. The method of claim 1, wherein said light scatter measurement is performed using two angles of light scatter signals.

3. The method of claim 2, wherein said two angles of light scatter signals are low angle light scatter signals detected in less than 10°.

4. The method of claim 3, wherein said one low angle light scatter signal is in a range from about 0° to about 4°.

5. The method of claim 4, wherein said another low angle light scatter signal is in a range from about 3° to about 7°.

6. The method of claim 1, wherein said light scatter measurement is performed using low angle light scatter signals detected in less than 10°.

7. The method of claim 1, wherein reporting of said nucleated red blood cells is in the form of reporting the number of nucleated red blood cells per one hundred leukocytes, or an absolute number of nucleated red blood cells per unit volume of said blood cell sample.

8. The method of claim 1, wherein said blood sell sample includes peripheral blood of a human, peripheral blood of a non-human, bone marrow of a human or bone marrow of a non-human.

9. A method for differentiating nucleated red blood cells and leukocytes comprising:
   (a) exposing a blood cell sample to a reagent system to lyse mature red blood cells without damaging leukocytes;
   (b) analyzing said sample in a flow cell by DC and light scatter measurements to differentiate nucleated red blood cells and leukocyte subpopulations; and
   (c) reporting nucleated red blood cells and leukocyte subpopulations in said blood cell sample.

10. The method of claim 9, wherein said light scatter measurement for differentiating nucleated red blood cells is performed using two angles of light scatter signals.

11. The method of claim 10, wherein said two angles of light scatter signals are low angle light scatter signals detected in less than 10°.

12. The method of claim 11, wherein said one low angle light scatter signal is in a range from about 0° to about 4°.

13. The method of claim 12, wherein said another low angle light scatter signal is in a range from about 3° to about 7°.

14. The method of claim 9, wherein said light scatter measurement for differentiating nucleated red blood cells is performed using low angle light scatter signal detected in less than 10°.

15. The method of claim 9, wherein said leukocyte subpopulations are selected from the group consisting of lymphocytes, monocytes, neutrophils and eosinophils.

16. The method of claim 9, wherein reporting of said leukocyte subpopulations is in absolute count per unit volume of said blood sample or in percentage of total leukocytes in said blood sample.

17. The method of claim 9, wherein reporting of said nucleated red blood cells is the form of reporting the number of nucleated red blood cells per one hundred leukocytes, or an absolute number of nucleated red blood cells per unit volume of said blood cell sample.

18. The method of claim 9, wherein said blood cell sample includes peripheral blood of a human, peripheral blood of a non-human, bone marrow of a human and bone marrow of a non-human.

* * * * *